May 30, 1972 W. T. HONEYCUTT Plant Pat. 3,200
WALNUT TREE
Filed Dec. 24, 1970
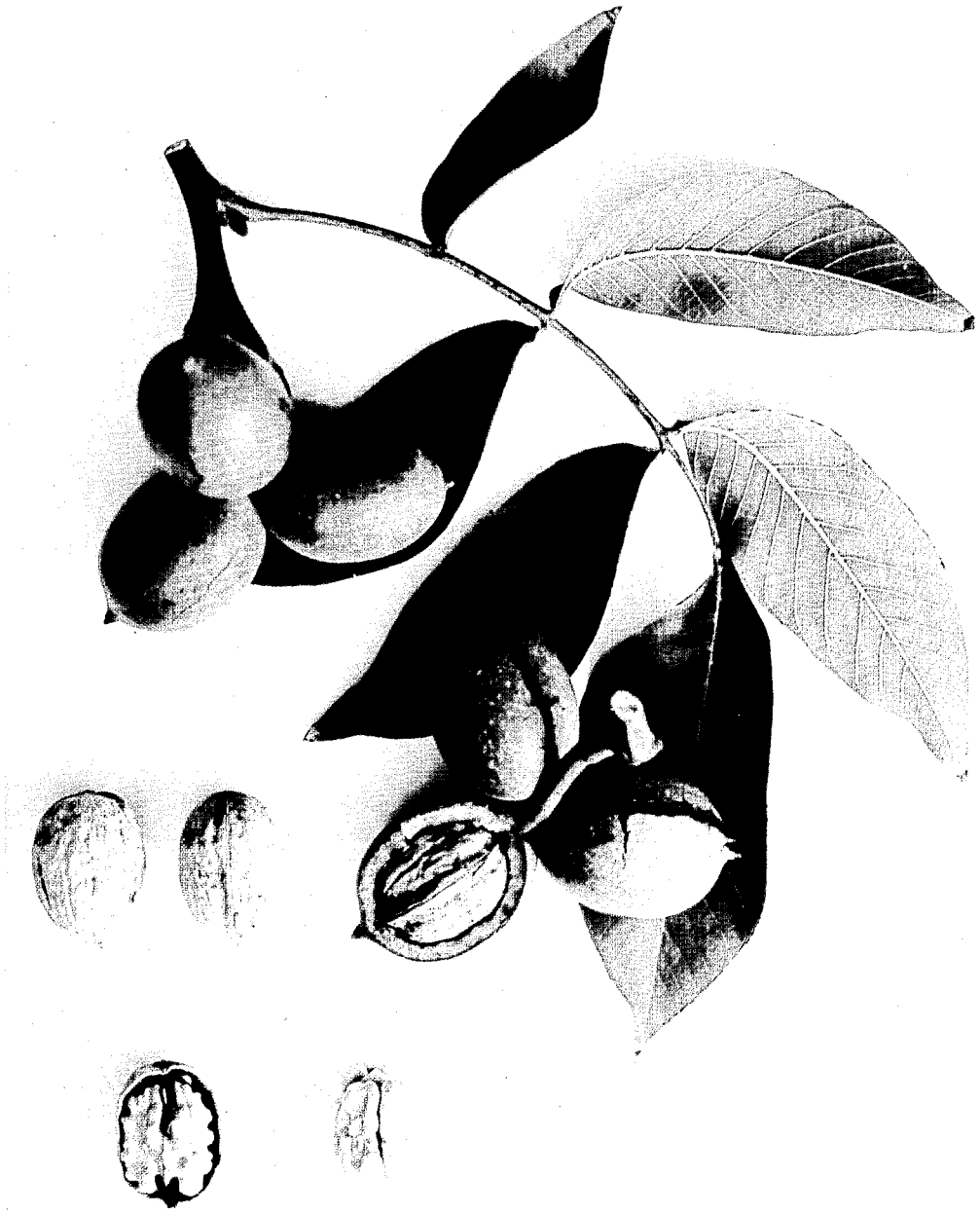
INVENTOR
William T. Honeycutt
BY
Webster & Webster
ATTORNEYS

United States Patent Office

Plant Pat. 3,200
Patented May 30, 1972

3,200
WALNUT TREE

William Thornton Honeycutt, 2918 Baker Road, Modesto, Calif. 95351

Filed Dec. 24, 1970, Ser. No. 101,446
Int. Cl. A01h 5/03
U.S. Cl. Plt.—32 1 Claim

ABSTRACT OF THE DISCLOSURE

A large, vigorous, medium dense, English walnut tree having abundant foliage, large compound leaves with long petioles, and early leafing and flowering; the tree being a regular and heavy producer of large, light color, well distributed nuts in harvest approximately with the payne (unpatented), and the nuts—averaging better than two in the clusters—having unusually long stems, hulls which open freely and widely, and kernels which exceed fifty percent of the whole nut weight.

*Origin of the variety*

I planted nursery-grown Eureka (unpatented) walnut trees in an orchard on my ranch located near Modesto, Stanislaus County, Calif., and when such orchard began nut production, I observed that one tree evidenced certain new and distinct, as well as commercially desirable, characteristics.

*Asexual reproduction of the variety*

In contemplation of ultimate commercial growing of the variety, discovered by me as aforesaid, I asexually reproduced it by grafting scions from the parent tree on Payne walnut trees—growing in the aforesaid orchard—which had been cut back in preparation for such grafting. Such reproductions, in maturity, ran true to the parent tree in all respects.

*Summary of the variety*

The present variety is a large, vigorous, medium dense, English walnut tree having abundant foliage, large compound leaves with long petioles, and early leafing and flowering; the tree being a regular and heavy producer of large, light color (almost shiny), well distributed nuts in harvest approximately with the Payne, and the nuts—averaging better than two in the clusters—having unusually long stems which cause easy release when the tree is shaken, and in maturity the hulls opening fully and widely so that the nuts are quite loose and which promotes natural drying and prevention of internal mold.

The present variety of walnut tree is further characterized by nuts wherein the percentage of kernel to nut, by weight, approximates, on the average, 51.4 percent.

In comparison to the Eureka, nuts of the present variety are generally similar but substantial distinctions exist in that spring starting, and harvesting, are both earlier, production is more consistent, the nut stem is longer, more multiples occur, nut color is lighter, and there is an absence of tip shrivel and frequent blanks both problems to which the Eureka is subject.

*Brief description of the drawing*

The drawing is a photographic reproduction in color of a twig, together with clusters of nuts; nuts out of hull; a nut with a portion of the shell removed to expose the meat; and a whole meat removed from the shell.

*Description of the variety*

The botanical details of this new and distinct variety of walnut tree—with color definitions (except those in common color terms) referenced to Maerz and Paul Dictionary of Color—are as follows:

Tree:
- *Size (at maturity).*—Large.
- *Vigor.*—Vigorous.

Trunk:
- *Form.*—Stocky.
- *Texture.*—Smooth.
- *Bark.*—Light.

Branches:
- *Form.*—Medium.
- *Texture.*—Smooth.
- *Lenticels.*—Medium number; medium size.
- *Branching habit.*—Spreading.
- *Color.*—New wood.—Grayish green. Mature wood—Brownish gray.

Foliage:
- *Quantity.*—Abundant.
- *Density.*—Medium.

Leaves:
- *Compound leaves.*—Size—large; average length—20"; average width—16". Petiole—long. Time of leafing—very early.
- *Leaflets.*—Size—large; average length—4"; average width—2½". Shape—lanceolate; acutely pointed. Thickness—thin. Texture—smooth. Margin—smooth. Petiole—long. Glands—lacking. Stipules—lacking. Color—top side—medium green (23–J–8); underside—lighter green (22–L–5).

Flowering habit:
- *Age at which tree starts producing catkins.*—Early.
- *Number of catkins produced.*—Average.
- *Size of catkins.*—Large.
- *Time of pollen shedding.*—Very early.
- *Age at which tree starts producing pistillate flowers.*—Very early.
- *Number of pistillate flowers produced by young trees.*—Abundant.
- *Number of pistillate flowers produced by mature trees.*—Abundant.
- *Percentage of lateral buds on long shoots (about 3 feet) of previous season's growth which produce pistillate flowers.*—Average—18%.
- *Number of pistillate flowers per inflorescence.*—Avage—3.
- *Time when pistillate flowers are receptive.*—Very early.
- *Coincidence of staminate and pistillate bloom.*—Good.

Crop:
- *Bearing.*—Regular bearer.
- *Productivity.*—Heavy.
- *Ripening period.*—Very early; about with Payne; slightly earlier than Eureka.
- *Evenness of maturity (period between time first and last nuts are ready to harvest).*—Short.
- *Quality.*—Good.
- *Distribution of nuts on tree.*—Well distributed throughout entire tree.
- *Tenacity.*—Tendency to drop off early; easy to harvest; easy to hull.

Hull:
- *Outer surface.*—Smooth.
- *Form.*—Regular.
- *Thickness.*—Thick.
- *Flesh.*—Fleshy.
- *Suture.*—Flat.
- *Dehiscence.*—Opens freely.
- *Splitting.*—Along suture; freely at base.

*Color.*—Yellowish green (21–K–7), spotted with gray-green.

Nut:

*Size.*—Large; average length—1⅞"; average diameter in suture plane—1¼"; average diameter cheek to cheek—1 5/16".

*Uniformity of size.*—Little variation.

*Form.*—Long cylindrical.

*Blossom end.*—Acuminate; asymmetrical.

*Basal end.*—Rounded.

*Weight.*—Weight of ten nuts—140 gr.; weight of ten kernels—72 gr.; average percentage kernel to nut—51.4.

*Thickness of shell.*—Medium thick.

*Hardness of shell.*—Hard.

*Seal of shell.*—Very good.

*Roughness of shell.*—Medium.

*Fill.*—Good.

*Color.*—Light beige (12–C–5).

Kernel:

*Size.*—Large.

*Plumpness.*—Plump.

*Shrivel.*—None.

*Speckling.*—Lightly.

*Veining.*—Lightly.

*Flavor.*—Good.

*Color (kernel from fresh nut).*—Yellowish light tan (11–I–4).

Resistance to disease: Good.

Resistance to insects: Good.

The walnut tree and its nuts herein described may vary in slight detail due to climatic and soil conditions under which the variety may be grown; the present description being of the variety as grown in the Central Valley of California.

I claim:

1. A new and distinct variety of English walnut tree, substantially as illustrated and described, which is large, vigorous, medium dense, abundant of foliage, with large compound leaves having long petioles, early in leafing and flowering, and a regular and heavy producer of large, light color, well distributed nuts which harvest about with the Payne; the nuts averaging more than two in the clusters, having unusually long stems, and hulls which open freely and widely; the percentage by weight of kernel to nut approximating, on the average, in excess of fifty percent, and—in comparison to the Eureka—the spring starting, and harvest, of the nuts are both earlier, production is more consistent, the nut stem is longer, more multiples occur, nut color is lighter, and there is an absence of tip shrivel and frequent blanks.

No references cited.

ROBERT E. BAGWILL, Primary Examiner